(12) United States Patent  
Spector

(10) Patent No.: US 9,910,425 B2
(45) Date of Patent: Mar. 6, 2018

(54) METHOD FOR CREATING CUSTOM ORTHOPEDIC SUPPORTS FROM COMPUTERIZED DATA INPUTS

(71) Applicant: Donald Spector, New York, NY (US)

(72) Inventor: Donald Spector, New York, NY (US)

(*) Notice: Subject to any disclaimer, the term of this patent is extended or adjusted under 35 U.S.C. 154(b) by 0 days.

(21) Appl. No.: 15/252,892

(22) Filed: Aug. 31, 2016

(65) Prior Publication Data

US 2017/0017230 A1   Jan. 19, 2017

Related U.S. Application Data

(63) Continuation-in-part of application No. 14/666,412, filed on Mar. 24, 2015, now abandoned, which is a
(Continued)

(51) Int. Cl.
| | |
|---|---|
| G05B 19/02 | (2006.01) |
| G05B 19/4099 | (2006.01) |
| A43B 7/14 | (2006.01) |
| A43B 7/24 | (2006.01) |
| A43B 17/00 | (2006.01) |
| A61B 6/00 | (2006.01) |
| A61B 5/107 | (2006.01) |
| A43D 1/02 | (2006.01) |

(Continued)

(52) U.S. Cl.
CPC .......... *G05B 19/4099* (2013.01); *A43B 7/141* (2013.01); *A43B 7/24* (2013.01); *A43B 17/00* (2013.01); *A43B 17/006* (2013.01); *A43D 1/025* (2013.01); *A61B 5/1072* (2013.01); *A61B 6/50* (2013.01); *A61B 6/505* (2013.01); *A61B 6/5217* (2013.01); *A61F 5/14* (2013.01); *B33Y 80/00* (2014.12); *G05B 15/02* (2013.01); *A43D 2200/60* (2013.01); *G05B 2219/49023* (2013.01)

(58) Field of Classification Search
None
See application file for complete search history.

(56) References Cited

U.S. PATENT DOCUMENTS 3,791,375 A   2/1974  Pfeiffer
3,974,491 A   8/1976  Sipe
(Continued)

FOREIGN PATENT DOCUMENTS

GB    2 300 919 A    11/1996

OTHER PUBLICATIONS

Gurney, "Review: Leg length Discrepancy", 2002, Elsevier, Gait and Posture 15 (2002), pp. 195-206.*
(Continued)

*Primary Examiner* — Jason Lin
(74) *Attorney, Agent, or Firm* — Collard & Roe, P.C.

(57) ABSTRACT

Systems and methods of measuring feet and designing and creating orthopedic inserts are described. A leg length discrepancy of a user is measured and this data, along with foot size are input into a computer. The computer then creates a computer model of a custom shoe insert based on this information. The computer model is then sent to a 3D printer to print the insert. The insert consists of a base insert with partial correction, and several additional layers that are added successively over time until a full correction is obtained. This eliminates any pain associated with a fully corrective insert, and allows the body to adjust gradually to the correction.

3 Claims, 4 Drawing Sheets

Related U.S. Application Data continuation-in-part of application No. 14/030,081, filed on Sep. 18, 2013, now Pat. No. 9,020,626, which is a continuation of application No. 11/737,454, filed on Apr. 19, 2007, now Pat. No. 8,583,272, which is a continuation-in-part of application No. 11/408,769, filed on Apr. 21, 2006, now abandoned.

(51) Int. Cl.
   *A61F 5/14* (2006.01)
   *G05B 15/02* (2006.01)
   *B33Y 80/00* (2015.01)

(56) References Cited

U.S. PATENT DOCUMENTS

| | | |
|---|---|---|
| 4,517,696 A | 5/1985 | Schartz |
| 4,647,918 A | 3/1987 | Goforth |
| 4,734,034 A | 3/1988 | Maness et al. |
| 4,745,930 A | 5/1988 | Confer |
| 4,813,436 A | 3/1989 | Au |
| 4,856,993 A | 8/1989 | Maness et al. |
| 4,862,743 A | 9/1989 | Seitz |
| 4,876,758 A | 10/1989 | Rolloff et al. |
| 5,033,291 A | 7/1991 | Podoloff et al. |
| 5,079,949 A | 1/1992 | Tamori |
| 5,088,503 A | 2/1992 | Seitz |
| 5,237,520 A | 8/1993 | White |
| 5,253,656 A | 10/1993 | Rincoe et al. |
| 5,323,650 A | 6/1994 | Fullen et al. |
| 5,394,626 A | 3/1995 | Brown |
| 5,449,002 A | 9/1995 | Goldman |
| 5,449,256 A | 9/1995 | Sundman |
| 5,593,699 A | 1/1997 | Grassi |
| 5,640,779 A | 6/1997 | Rolloff et al. |
| 5,678,448 A | 10/1997 | Fullen et al. |
| 5,790,256 A | 8/1998 | Brown et al. |
| 5,945,610 A | 8/1999 | Galasso |
| 6,000,082 A | 12/1999 | Nguyen |
| 6,026,351 A | 2/2000 | Takeuchi |
| 6,141,889 A | 11/2000 | Baum |
| 6,195,921 B1 | 3/2001 | Truong |
| 6,216,545 B1 | 4/2001 | Taylor |
| 6,331,893 B1 | 12/2001 | Brown et al. |
| 6,360,597 B1 | 3/2002 | Hubbard, Jr. |
| 6,463,351 B1 | 10/2002 | Clynch |
| 6,735,547 B1 | 5/2004 | Yfantis |
| 6,804,571 B2 | 10/2004 | Fullen et al. |
| 6,823,550 B2 | 11/2004 | Kantro |
| 7,008,386 B2 | 3/2006 | Alaimo et al. |
| 7,199,866 B2 | 4/2007 | Gogolla et al. |
| 7,206,718 B2 | 4/2007 | Cavanagh et al. |
| 7,346,418 B2 | 3/2008 | Lowe |
| 7,402,148 B2 | 7/2008 | Brewer |
| D577,478 S | 9/2008 | Peveto et al. |
| 7,617,068 B2 | 11/2009 | Tadin et al. |
| 7,661,170 B2 | 2/2010 | Goode et al. |
| 8,036,768 B2 | 10/2011 | Lowe |
| 8,117,922 B2 | 2/2012 | Xia et al. |
| 8,170,705 B2 | 5/2012 | Koelling et al. |
| 8,290,739 B2 | 10/2012 | Tadin et al. |
| 8,819,961 B1 | 9/2014 | Ellis |
| 2001/0047194 A1 | 11/2001 | Thompson et al. |
| 2003/0179362 A1 | 9/2003 | Osawa et al. |
| 2003/0191554 A1 | 10/2003 | Russell et al. |
| 2004/0029639 A1 | 2/2004 | Regan |
| 2004/0044296 A1 | 3/2004 | Linton |
| 2004/0133431 A1 | 7/2004 | Udiljak et al. |
| 2004/0143452 A1 | 7/2004 | Pattillo et al. |
| 2004/0168329 A1 | 9/2004 | Ishimaru |
| 2006/0017021 A1 | 1/2006 | Yoda et al. |
| 2007/0033750 A1 | 2/2007 | Cook et al. |
| 2007/0055405 A1 | 3/2007 | Koelling et al. |
| 2007/0118243 A1 | 5/2007 | Schroeder et al. |
| 2007/0250287 A1 | 10/2007 | Spector |
| 2008/0010861 A1* | 1/2008 | Kosmas ............... A43B 7/142 36/91 |
| 2010/0161076 A1 | 6/2010 | Pallari |
| 2010/0262239 A1* | 10/2010 | Boyden ............... A61B 17/68 623/16.11 |
| 2014/0309692 A1* | 10/2014 | Mor ............... A43B 7/144 606/237 |
| 2016/0046074 A1* | 2/2016 | Jang ............... B29C 67/0088 700/119 |

OTHER PUBLICATIONS

International Preliminary Report on Patentability and Written Opinion of the International Searching Authority of PCT/US07/67052, dated Apr. 1, 2008.

\* cited by examiner

METHOD FOR CREATING CUSTOM ORTHOPEDIC SUPPORTS FROM COMPUTERIZED DATA INPUTS

STATEMENT OF RELATED CASES

This application is a continuation in part of U.S. patent application Ser. No. 14/666,412 filed on Mar. 24, 2015, which is a continuation-in-part of U.S. patent application Ser. No. 14/030,081 filed Sep. 18, 2013 (now U.S. Pat. No. 9,020,626), which is a continuation of U.S. patent application Ser. No. 11/737,454 filed Apr. 19, 2007 (now U.S. Pat. No. 8,583,272), which is a continuation-in-part of U.S. patent application Ser. No. 11/408,769 filed Apr. 21, 2006, all of which are incorporated herein by reference.

BACKGROUND OF THE INVENTION

This product relates to the field of orthopedic inserts for shoes, sneakers and other footwear.

These product lines are typically divided into two categories. One such category is defined by relatively universal insoles that cushion and provide general support. A previous patent discloses the first adjustable insole, in which the bounce of the insole can be controlled by turning a valve. Other products on the market are those such as manufactured under the brand name Dr. Scholl's.

Most of these products tend to be for comfort or support and are universal in use. They are relatively inexpensive.

At the other end of the spectrum are the devices referred to as supports. These are often made by Podiatrists. Podiatrists take imprints and casts of people's feet and then have inserts designed that are made to correct the weight and imprint of the foot. These inserts are often used to correct for leg length discrepancy (LLD). LLD can often lead to scoliosis, a curvature in the spine. For adolescents going through a growth period, it would be desirable to attempt to prevent and/or treat this scoliosis using progressive foot orthotics.

SUMMARY OF THE INVENTION

One aspect of the present invention is a method of assessing a patient's spinal deformity and/or leg length discrepancy and developing an orthopedic insert to correct for this deformity. This insert can then be attached to shoes or other inserts which correct for other foot problems, such as over- or under-pronation, plantar fasciitis, etc. The invention includes measuring the spinal column and/or legs using any desired method, such as by digital X-ray, measuring the patient's feet by any suitable method, and manufacturing the orthopedic insert based on the design. In particular, the manufacturing method includes manufacturing a series of graduated inserts that are used over time to gradually correct for the spinal deformity.

The system, in accordance with one aspect of the present invention, includes measuring and analyzing the spinal column and leg length using digital X-rays, and communicating the data regarding any spinal deformity or LLD to a computer that then designs an orthopedic insert for printing on a 3D printer. The patient's foot size and shape are also measured and input into the computer. The analysis and the making of the orthopedic insert are performed automatically after measuring. The system can be programmed to create a series of graduated inserts that start off with only minor corrective features, and then build up to full correction over time, to minimize pain and hopefully permanently correct any spinal curvature as the adolescent grows.

In a preferred embodiment, the inserts are created as a series of layers on a base insert. For example, the base insert with a first level of correction is printed, and the user will wear that insert for a specified period of time. Then, when further correction is desired, an additional layer is printed, which is then attached to the base insert. Further layers can be added over time until the full correction has been achieved. These layers can be printed out as needed, or a full set of all of the layers can be printed in a single printing process, and the user can then add the layers to the base insert as needed. The insert and layers can be made of the same material, or the base insert can be made of a different material from the additional layers. Any suitable material for making the inserts and layers could be used.

DESCRIPTION OF THE EMBODIMENTS

One object of this invention to create a collateral informational base that is immediately capable of altering the manufacture of inserts on a personal basis in an economic way. This can be particularly important since the cost of inserts by podiatrists typically cost hundreds of dollars, for an end product that probably has a cost of goods of only a few dollars. The computerized instructions for the manufacturing of the insert can be transmitted to a foreign country where these inserts can be made by hand or eventually transmitted to machines that can actually create three dimensional moldings that can then be sold to the consumers at a faction of the cost of present inserts sold by Podiatrists.

It is believed that almost 90% of the population has two different size legs. Typically, people with two different size legs learn to compensate for this difference by favoring one side. Experts in the field have shown that this is a primary cause of scoliosis, back problems, hip problems as well as pain in later life. This problem can be immediately eliminated using instant 3D foot inserts in accordance with the various aspects of the present invention.

Traditionally, people have gone to podiatrists to make castings, and from these, to make inserts. This process costs several hundred dollars and requires multiple visits. Most people do not go through this effort and expense, unless they have severe problems. However, the chronic problems do not manifest as major problems until later, and are not detected until permanent damages has been done, for example, to the spinal column.

The present invention offers a simple, easy technology based on 3D printers that are connected to a computer platform to instantly read and identify problems with weight distribution and the size of a person's leg to automatically print out a plastic insert with multiple layers to build upon without the need for casts, multiple visits or large expense.

Figure 1:
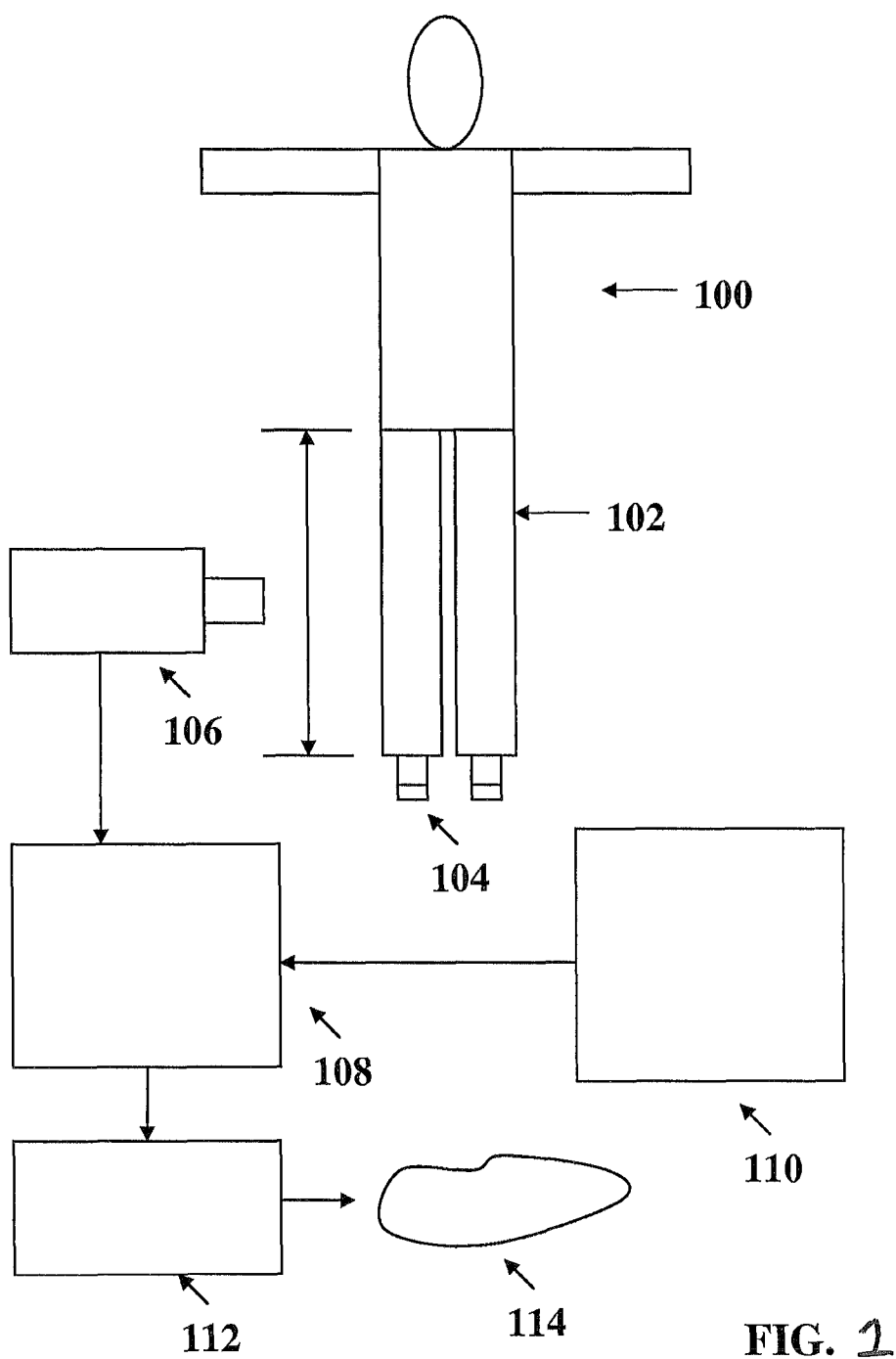
FIG. 1 illustrates the system according to the invention.

Referring to FIG. 1, one embodiment of the present invention is illustrated. A person 100 has two legs 102 and two feet 104. The length of the legs 102 and the spinal column curvature is measured and determined using a measuring device 106. The measuring device for the legs can be a laser or any other type of measuring device. For example, a simple tape measure could even be used. Digital X-rays could also be used for the LLD as well as spinal column. The length of the legs 102 or the discrepancy between the length of the legs, as well as any spinal curvature data is entered into a processor 108. Also entered into a processor 108 is the shoe size or footbed measurements. The footbed measurements can be taken with molds that are then scanned and input into the processor as well, or simply a shoe size can be entered, if additional foot corrections are unnecessary.

The information concerning the orthopedic inserts are transmitted from the processor 108 to a 3D printer 112, also known as a rapid prototyping machine. The 3D printer then instantly generates the necessary orthopedic insert or inserts 114. Insert 114 is custom made to compensate for the user's leg length discrepancy as well. The method of the present invention can be performed by a technician entering the leg length discrepancy information and shoe model information directly into a computer connected to the 3D printer, or can take place remotely. This information can then be used for configuration of the computer model and sent to the printer for printing the insert. The printer can be directly connected to the server or can be located remotely. In the remote situation, the printer is connected to a processor which processes the information received from the server to configure the insert for printing. The server sends the data over the internet to the processor which then creates the computer model of the insert using the received data.

Figure 2:
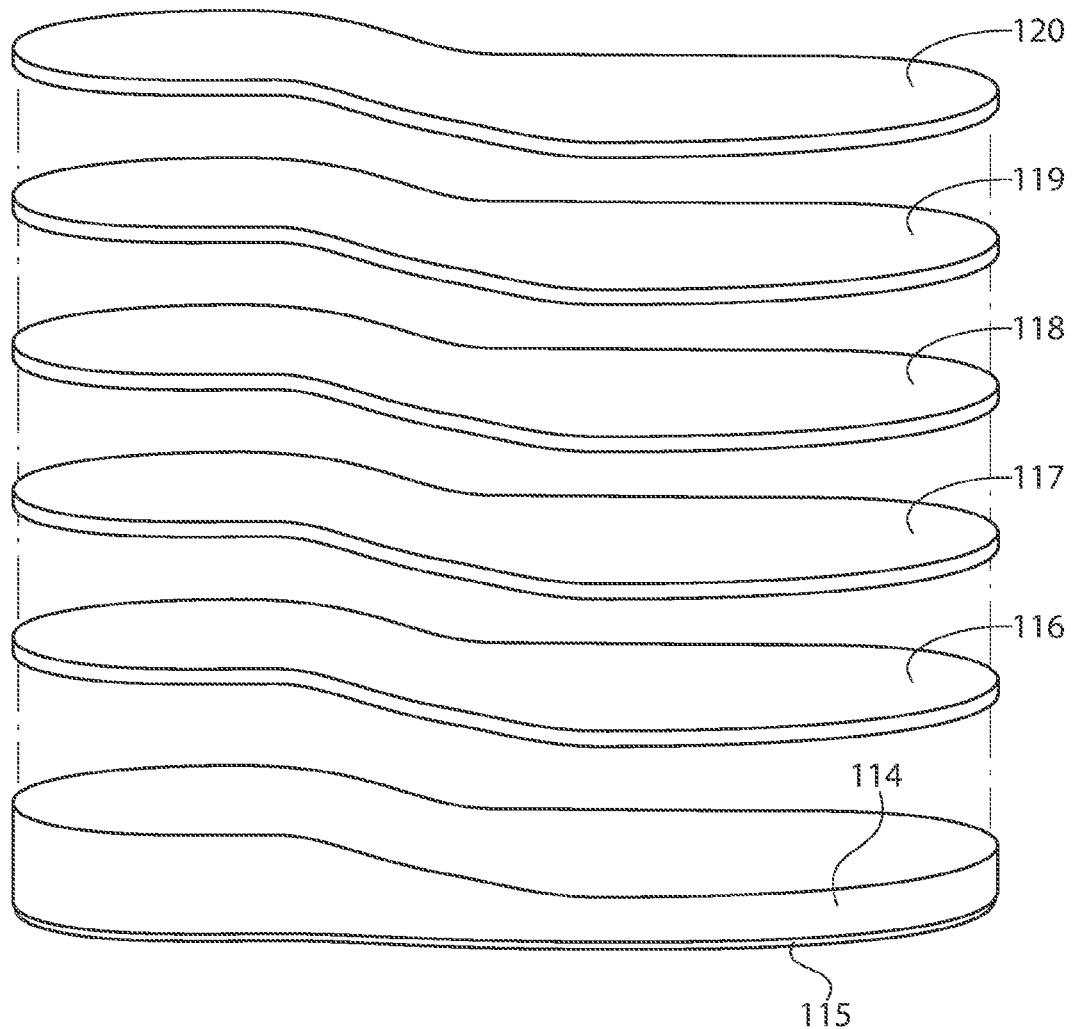
FIG. 2 illustrates a series of shoe inserts created with the method according to the invention.
Figure 3:
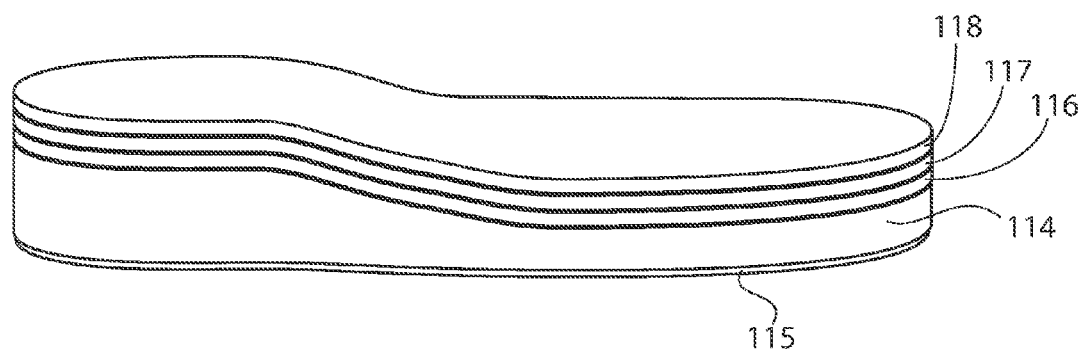
FIG. 3 illustrates a shoe insert created with the method according to the invention.

FIGS. 2 and 3 show the insert 114 according to the invention, and the various layers 116-120 which can be added on to the insert 114 over time. In one situation, insert 114 is printed initially and worn by the user over a period of time. The user then goes back for periodic checks to the doctor or technician that can print out individual layers 115-120, and adhere them to the original insert 114, to provide added correction. The user can continue the visits and checks, adding layers as needed until full correction has been obtained. Insert 114 can be provided with a layer of adhesive 115 for attaching it to a shoe. The additional layers can be placed over the base insert or over any part of the sole, even if it is not covered by the base insert.

Figure 4:
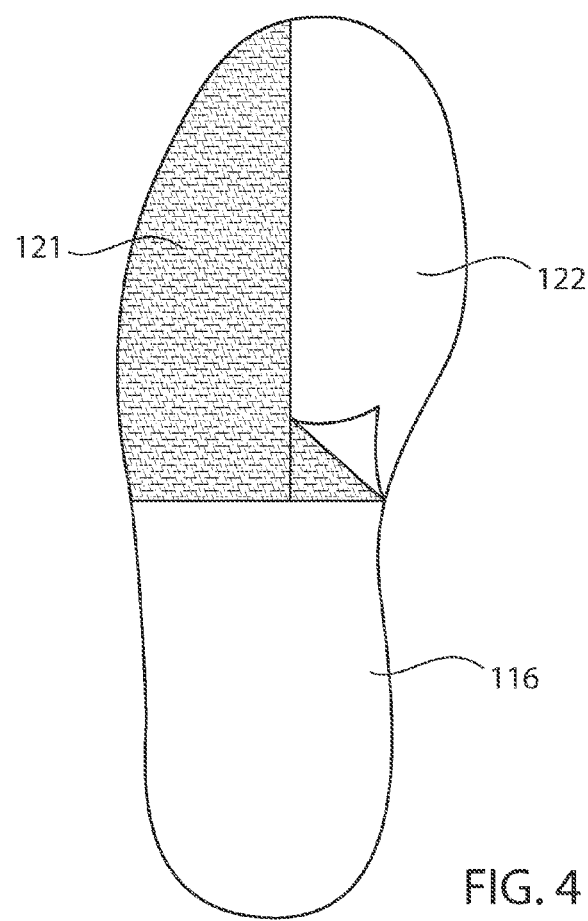
FIG. 4 illustrates a shoe insert having a layer provided with a layer of adhesive protected by a peel-off backing according to the invention.

In another situation, the insert and all layers 116-120 can be printed at once, and the users can add the individual layers 116-120 at their own discretion. As shown in FIG. 4, each layer 116-120 can be provided on a bottom surface with a layer of adhesive 121 protected by a peel-off backing 122. Alternatively, a liquid adhesive (not shown) can be applied to each layer during application.

The layers can be created with any type of correction in mind, and each layer can have a different shape if needed. The computer can be programmed to create an overall system for correction of anatomical defects in accordance with medical guidelines, so that different aspects are treated at different times. For example, the forefoot and arch could be treated in some layers, with more heel lifting occurring in other layers. Alternatively, each layer can be the same and add height in a uniform manner.

Figure 5:
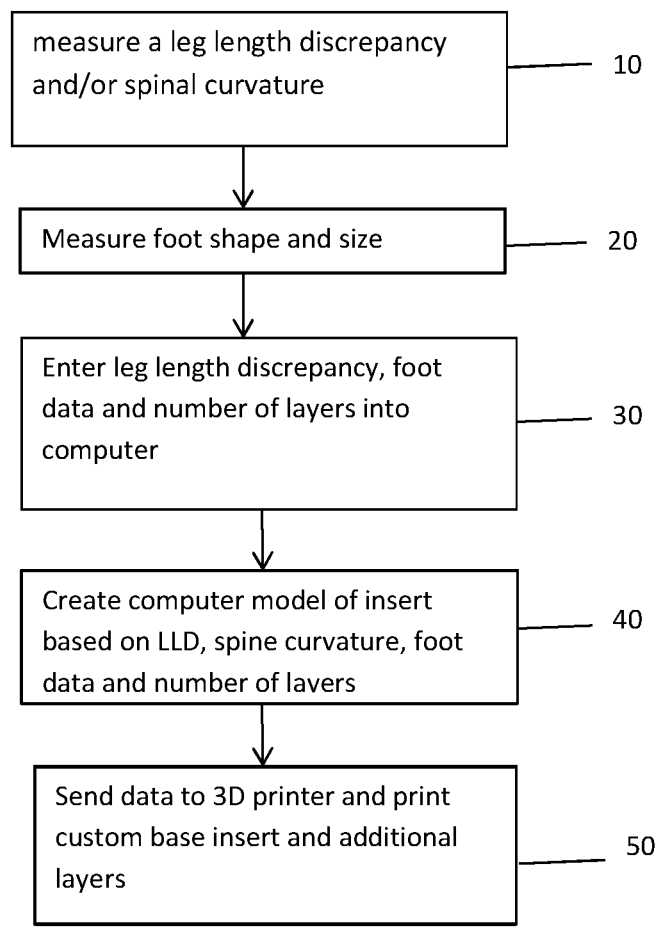
FIG. 5 illustrates the method steps for creating a shoe insert according to the invention.

FIG. 5 illustrates the method steps according to the invention.

In step 10, a user measures a leg length discrepancy and/or spinal curvature using any desired method: tape measure, X-ray, laser, etc. In step 20, the foot shape and size are measured using any conventional method. The amount of leg length discrepancy and spinal curvature data is entered into processor 108 by the user in step 30, along with the foot shape/size data and the number of separate insert layers to be created.

In step 40, processor 108 takes the leg length discrepancy data and configures a computer model for a custom insert for the user. This custom insert consists of a base insert plus successive layers to be added over time, resulting finally in a complete insert that offers a full corrective effect.

In step 50, this computer model is then sent to printer 112 for printing the actual insert and separate layers. The printer 112 can be programmed to print only one insert or layer at a time upon individual commands by the operator to the printer, or can be print the base insert with all of the layers in one printing run. In the instance where separate layers are printed individually, the processor stores the information regarding the insert and layers in the database, and keeps track of which layers have already been printed, so the next successive layer is queued up to print upon a command by the operator. Thus, a completely custom insert with successive corrective layers can be made quickly and inexpensively.

While there have been shown, described and pointed out fundamental novel features of the invention as applied to preferred embodiments thereof, it will be understood that various omissions and substitutions and changes in the form and details of the device illustrated and in its operation may be made by those skilled in the art without departing from the spirit of the invention. It is the intention, therefore, to be limited only as indicated by the scope of the claims appended hereto.

What is claimed is:

1. A method of developing at least one orthopedic insert for footwear used by a person, the method comprising:
    measuring and analyzing a spinal column and leg length of the person using digital X-rays;
    measuring a foot size and shape of a person;
    receiving in a computer data defining spinal abnormalities and leg length discrepancy as well as foot size and shape of the person;
    designing in the computer via a processor a computer model of an orthopedic insert based on the data input to the computer, the orthopedic insert comprising a base insert having a partial corrective effect and a plurality of separate layers to be applied on top of the base insert, each one of said plurality of separate layers being configured to achieve a further corrective effect when applied on top of the base insert;
    transmitting the computer model of the orthopedic insert from the computer to a manufacturing device comprising a 3D printer; and
    making the orthopedic insert comprising the base insert and and plurality of separate layers with the manufacturing device based on the computer model in a single printing process, applying adhesive to each one of the plurality of separate layers, and applying a peel-off backing to the adhesive on each one of the separate layers, so that the separate layers can be applied to the base layer at later times.

2. The method according to claim 1, wherein the steps of receiving include receiving the data regarding leg length discrepancy and foot size via a transmission over the internet.

3. The method according to claim 1, wherein the step of receiving includes receiving data regarding a number of additional layers to be manufactured for attachment to the base insert.

* * * * *